US012678791B2

(12) United States Patent
Guzman et al.

(10) Patent No.: US 12,678,791 B2
(45) Date of Patent: Jul. 14, 2026

(54) INTEGRATED MODULAR ON-CHIP DROPLET MICROFLUIDIC SCREENING PLATFORM

(71) Applicant: The Texas A&M University System, College Station, TX (US)

(72) Inventors: Adrian R. Guzman, Houston, TX (US); Arum Han, College Station, TX (US); Paul J. de Figueiredo, Bryan, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 1177 days.

(21) Appl. No.: 16/963,324

(22) PCT Filed: Jan. 25, 2019

(86) PCT No.: PCT/US2019/015260
§ 371 (c)(1),
(2) Date: Jul. 20, 2020

(87) PCT Pub. No.: WO2019/148013
PCT Pub. Date: Aug. 1, 2019

(65) Prior Publication Data
US 2020/0360929 A1 Nov. 19, 2020

Related U.S. Application Data

(60) Provisional application No. 62/623,344, filed on Jan. 29, 2018.

(51) Int. Cl.
*B01L 3/00* (2006.01)
*C12M 1/00* (2006.01)
*C12M 3/06* (2006.01)

(52) U.S. Cl.
CPC ... *B01L 3/502784* (2013.01); *B01L 3/502707* (2013.01); *C12M 23/16* (2013.01);
(Continued)

(58) Field of Classification Search
CPC ......... B01L 3/502784; B01L 3/502707; B01L 2200/0652; B01L 2200/0668;
(Continued)

(56) References Cited

U.S. PATENT DOCUMENTS

2010/0297733 A1* 11/2010 Lin .......................... C07K 1/14
435/325
2011/0059556 A1 3/2011 Strey
(Continued)

OTHER PUBLICATIONS

"3D Printing Process" from Markforged, https://web.archive.org/web/20201125114122/https://markforged.com/resources/learn/3d-printing-basics/how-do-3d-printers-work/3d-printing-process, retrieved using WayBack Machine (Year: 2020).*
(Continued)

*Primary Examiner* — Melvin C. Mayes
*Assistant Examiner* — Sophia Y Lyle
(74) *Attorney, Agent, or Firm* — CONLEY ROSE, P.C.

(57) ABSTRACT

An automated fully integrated on-chip ultra-high-throughput droplet microfluidic screening platform (PolyChip) has been developed that integrates the cultivation and manipulation of cells (e.g., microbial) communities with "on the fly" sorting and analyses. The PolyChip system enables continuous operation of the entire process, from cell-encapsulated droplet generation, culture, merging with other cell-encapsulated droplets, culture, merging with reagent-laden droplets, culture, followed by detection and sorting.

20 Claims, 3 Drawing Sheets

(52) U.S. Cl.
CPC ...... *C12M 47/04* (2013.01); *B01L 2200/0652* (2013.01); *B01L 2200/0668* (2013.01)

(58) Field of Classification Search
CPC ..... B01L 2200/0673; B01L 2300/0874; B01L 2300/0887; C12M 23/16; C12M 47/04; C12M 35/08; C12M 25/16
See application file for complete search history.

(56) References Cited

U.S. PATENT DOCUMENTS

| | | | | |
|---|---|---|---|---|
| 2011/0312841 | A1* | 12/2011 | Silverbrook | C12Q 1/68 |
| | | | | 506/40 |
| 2013/0083315 | A1* | 4/2013 | Lo | G01J 3/46 |
| | | | | 356/402 |
| 2013/0260447 | A1* | 10/2013 | Link | C12Q 1/686 |
| | | | | 435/283.1 |
| 2014/0134631 | A1* | 5/2014 | Clime | G01N 35/00009 |
| | | | | 435/6.12 |
| 2015/0232942 | A1 | 8/2015 | Abate et al. | |

OTHER PUBLICATIONS

"Layer thickness in 3D printing: an additive manufacturing basic" from Sculpteo, https://web.archive.org/web/20160308173116/http://www.sculpteo.com/en/glossary/layer-thickness-definition, retrieved using WayBack Machine, Mar. 8, 2016 (Year: 2016).*

PCT/US2019/015260 International Search Report and Written Opinion dated Aug. 9, 2019 (14 p.).

Kim, Hyun Soo et al., "A Droplet Microfluidics Platform for Rapid Microalgal Growth and Oil Production Analysis," Biotechnology and Bioengineering, vol. 113, No. 8, Aug. 2016, pp. 1691-1701 (11 p.).

Kim, Hyun Soo et al., "High-Throughput Droplet Microfluidics Screening Platform for Selecting Fast-Growing and High Lipid-Producing Microalgae from a Mutant Library," Plant Direct, Sep. 2017, vol. 1, pp. 1-13 (14 p.).

* cited by examiner

INTEGRATED MODULAR ON-CHIP DROPLET MICROFLUIDIC SCREENING PLATFORM

CROSS-REFERENCE TO RELATED APPLICATIONS

This application is a 35 U.S.C. § 371 national stage application of PCT/US2019/015260 filed Jan. 25, 2019, and entitled "Integrated Modular On-Chip Droplet Microfluidic Screening Platform," which claims priority to U.S. Provisional Patent Application No. 62/623,344 filed on Jan. 29, 2018, each of which is hereby incorporated herein by reference in its entirety for all purposes.

GOVERNMENT FUNDING

This invention was made with government support under grant HDTRA1-12-1-0028 awarded by the Defense Threat Reduction Agency (DTRA). The government has certain rights in the invention.

FIELD

The disclosure relates generally to microfluidic devices. The disclosure relates specifically to microfluidic droplet screening platforms.

BACKGROUND

Microbes in the environment exist as members of complex communities, and interactions among these members regulate the survival, growth and persistence of individual microbial species. Many biothreat agents, including *Francisella, Coxiella,* and *Brucella,* can survive and persist in the environment. Moreover, many human opportunistic bacterial and fungal pathogens of clinical consequence, including *Salmonella enterica, Pseudomonas aeruginosa, Cryptococcus neoformans,* can survive or grow in distinct environmental niches. Release of antibiotics and antimicrobials into the environment also contribute to the emergence of anti-microbial or antibiotic resistant strains of fungal, parasitic, or bacterial pathogens, respectively. Therefore, gaining an understanding of interactions between microbes and their environments is of profound clinical importance. Here, the term "environment" is not limited to natural environments, but rather also include environments in animal, plant, and human, where microorganisms exist as members of complex communities (e.g., gut/skin/oral microbiota). In addition, interactions amongst these microorganisms in communities as well as their interactions with the surrounding environment (including mammalian cells) can also ensue synergistic activities, such as improved functions or more resilience and robustness. Unfortunately, the polymicrobial interactions that mediate these processes remain obscure. In addition, microbes (both cultured and uncultured) can serve as outstanding sources of novel antimicrobial compounds. In fact, some of the most successful antimicrobial products are naturally derived from microbes (e.g., Penicillin). Therefore, the development of systems that can facilitate the discovery of novel antimicrobials produced by microbes is of significant basic science, clinical, and commercial interest. The application of such systems is not limited to developing anti-bacterial or anti-fungal products against human or animal pathogens, but is also relevant to developing anti-bacterial or anti-fungal products against pathogens of terrestrial and aquatic plants. The application of the system can include, but is not limited to, targeting cell death, reduction in target cell growth compared to normal growth, activation of nucleic acid expression, suppression of nucleic acid expression, activation of protein expression, suppression of protein expression, activation of metabolic product expression, or suppression of metabolic product expression The system can contribute to including, but not limited to, crop protection, environmental remediation, water treatment, and waste storage and disposal. Microbe-host and microbe-microbe interactions are critical in understanding microbiome dynamics. Therefore, systems that can elucidate such dynamics are of significant interest to the microbiome and microbiome-host interaction research and clinical communities. Finally, interactions that have synergistic activities can be utilized in diverse microbial bioproduction and bioremediation applications with higher efficiency and higher robustness. Thus, overall, understanding the interactions between microorganisms and testing such interactions rapidly can have enormous benefit.

SUMMARY

An embodiment of the disclosure is a multilayered droplet microfluidic platform comprising a plurality of substrate layers, and functional components fabricated in the substrate layers. The functional components comprise at least one droplet generator for continuous generation of cell-encapsulated droplets; at least one merging mechanism for merging of the cell-encapsulated droplets or releasable core-shell/multi-shell structure serving as a merging component; at least one incubation chamber for on-chip incubation of the cell-encapsulated droplets; at least one valve for trapping or releasing the cell-encapsulated droplets; a detection mechanism; and a mechanism for sorting of the cell-encapsulated droplets; at least one passage to connect the functional components and move droplets from one functional components to the other(s) functional component(s); wherein the platform is capable of continuous or semi-continuous on-chip operation in a first-in first-out manner.

In an embodiment, the multilayered droplet microfluidic platform further comprises a functional component for on-chip recovery of sorted cell-encapsulated droplets. In an embodiment, the on-chip detection mechanism comprises but is not limited to detecting fluorescence, colorimetric, dielectric, conductivity, or vibrational spectroscopy signals. In an embodiment, the optical detection mechanism comprises fluorescence or colorimetry. In an embodiment, the dielectric detection mechanism comprises impedance spectroscopy. In an embodiment, the vibrational spectroscopy signal comprises Raman spectroscopy or infrared spectroscopy. In an embodiment, the platform comprises about 9 to about 20 polydimethylsiloxane layers (or more, with no limitations). In an embodiment, the platform comprises a sandwich design wherein droplets are stacked in a top-down format and travel vertically from a higher layer of the platform to a lower layer of the platform (or from a lower layer to a higher layer). In an embodiment, the platform comprises a stacked design wherein droplets traverse the platform without traveling vertically to a lower layer of the platform. In an embodiment, dead volume has been eliminated or minimized.

An embodiment of the disclosure is a method of producing a multilayered droplet microfluidic platform comprising: casting about 9 to about 20 (or more, with no limitations) individual polydimethylsiloxane layers using master molds; and bonding the individual layers into a single structure comprising a network of fluid channels and functional components between adjacent layers; alternatively manufactured through injection molding; wherein the platform is capable of continuous or semi-continuous on-chip operation through a sequence of functional components in a first-in first-out manner.

An embodiment of the disclosure is a method to isolate each functional component in a multilayered droplet microfluidic platform through one or more integrated microvalve to control the flow of droplets so that each functional component can be operated independent of each other, to minimize the effect of one functional component impacting the operating condition of the other connected functional components.

An embodiment of the disclosure is a method for identifying cell-produced molecules affecting a target cell utilizing a multilayered droplet microfluidic platform, comprising: generating continuously a first group of cell-encapsulated droplets from a library of cells that are potential producers of a molecule capable of affecting a target cell; incubating the first group of generated cell-encapsulated droplets to provide time for the molecules produced by the cells to accumulate within droplets; generating a second group of cell-encapsulated droplets containing the target cells; merging of the first and second groups (or additional groups) of cell-encapsulated droplets to allow co-incubation of both cell types and to provide time for the produced molecules to influence the target cells; analyzing the cell-encapsulated droplets (including cells within them) using an on-chip detection mechanism; sorting the cell-encapsulated droplets based on the detection result; and recovering sorted cell-encapsulated droplets. In an embodiment, the recovering of the sorted cell-encapsulated droplets is on-chip or off-chip. In an embodiment, the on-chip analysis of the cell-encapsulated droplets comprises at least one selected from the group consisting of: determining expression or function of a nucleic acid or protein; analyzing the growth rate or apoptosis of a target cell; and evaluating metabolic activity or production of metabolic products. In an embodiment, the on-chip analysis of cell-encapsulated droplets further comprises a mechanism for the detection of fluorescent, colorimetric, dielectric, conductivity, or vibrational spectroscopy signals. In an embodiment, at least one of the following is detected: target cell death, reduction in target cell growth compared to normal growth, increase in target cell growth compared to normal growth, activation of nucleic acid expression, suppression of nucleic acid expression, activation of protein expression, suppression of protein expression, activation of metabolic product expression, or suppression of metabolic product expression. In an embodiment, the nucleic acid is mRNA or rRNA. In an embodiment, the protein is a fluorescent protein. In an embodiment, the metabolic product is a surfactant, drug lead, or lipid. In an embodiment, sorting occurs to cell-encapsulated droplets when adverse effects to the target cell are observed. In an embodiment, sorting occurs to cell-encapsulated droplets when synergistic effects to the target cell are observed. In an embodiment, the target cell comprises at least one selected from the group consisting of eukaryotic cells, bacterial cells, Archeal cells, pathogens, commensal organisms, microbes, mammalian cells, and insect cells. In an embodiment, the mammalian cells are human cells or animal cells. In an embodiment, the libraries screened comprise at least one selected from the group consisting of environmental microbes, synthetic libraries of microbes that produce diverse small molecules, and microbiota. In an embodiment, the environmental microbes comprise culturable and unculturable environmental microbes. In an embodiment, the microbiota comprises human-, animal-, or plant-associated microbiota. In an embodiment, the synthetic library is a polyketide expression library.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

Like elements in the various figures are denoted by like reference numerals for consistence.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary $3^{rd}$ Edition.

As used herein, the term "microfluidic device", "microfluidic platform", "chip", or "lab-on-chip" or LOC refers to a device, apparatus or system comprising a network of channels and other features that facilitate movement, manipulation, and analysis of cells, reagents, and cell-encapsulated droplets.

As used herein, the term "off-chip" refers to structures, modules, and other components that may be integrated with or connected to, but do not form part of, the microfluidic device, as well as the handling or processing of reagents off or outside of a microfluidic device.

As used herein, the term "continuous operation" refers to the formation and manipulation of cell-encapsulated droplets occurring on a single microfluidic platform without interruption in the flow, contrary to "stop-and-go operation" where one or more certain on-chip droplet operation has to be stopped for a particular assay to be completed.

As used herein, the term "semi-continuous operation" refers to the formation and manipulation of cell-encapsulated droplets occurring on a single microfluidic platform without interruption in the operation, but utilization of valves and multiplexed components to operate the platform in a segmented but continuous manner by switching operations from one segment of the device to an identical separate segment.

Figure 1:
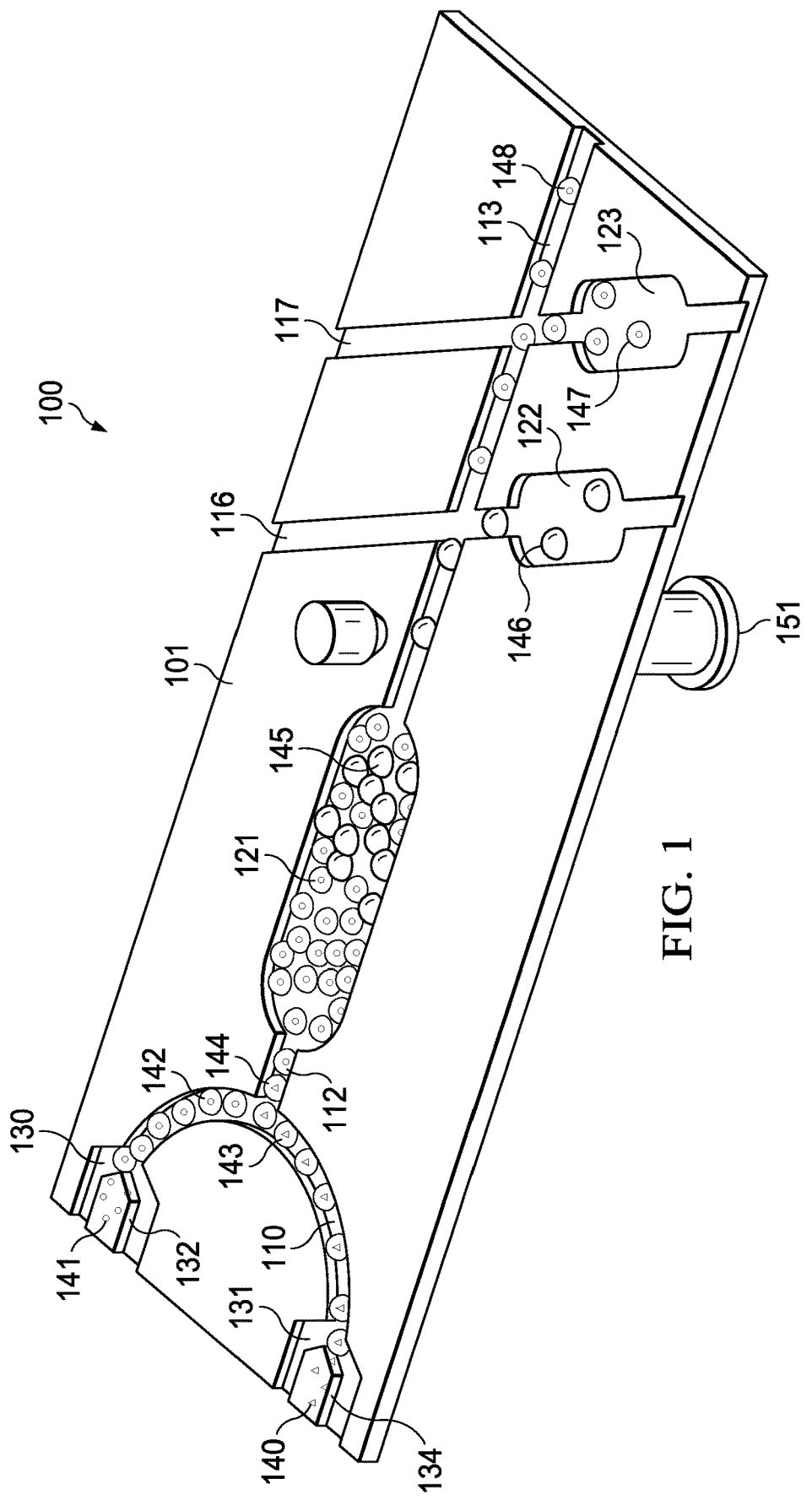
FIG. 1 Shows a conceptual framework of a droplet microfluidic chip in accordance with embodiments disclosed herein and named PolyChip.

Recent advances in lab-on-a-chip microfluidic systems have the potential to revolutionize the study of polymicrobial interactions. These microfluidic systems have the capability to manipulate extremely small volumes of samples with high precision and accuracy and using such capabilities to conduct complicated functional assays useful for biological studies at high throughput. In particular, droplet microfluidic systems have the potential to enable the simultaneous cultivation of millions of spatially distinct model microbial communities and probe their interactions and outcome, followed by sorting out the microbes or microbial communities of high interest. Such complex assays at high throughput are enabled by the capabilities to generate and manipulate droplets for cell encapsulation, reagent encapsulation, synchronization, merging, incubation, detection, splitting, and sorting. However, due to the complexity of fabrication, integration, and operation, these systems have not been employed to interrogate interactions between two or multiple sets of cells: (1) target cells against which bioactive molecules are tested; (2) library cells, which produce the bioactive compounds. In one embodiment, the target cells are pathogens or other antibiotic resistant microbes, and the library cells are microbes harvested from the environment or engineered to encode libraries of bioactive molecules. In addition, these droplet microfluidic systems have not been previously fully integrated into a single system that can conduct the entire multi-step process needed to perform functional assays (e.g., polymicrobial interactions) that enable downstream biological analyses. Here an automated fully integrated on-chip ultra-high-throughput droplet microfluidic screening platform (PolyChip) was developed that integrates the generation, co-cultivation, and manipulation of microbial communities with "on the fly" detection, sorting, and analyses through a continuous flow process to handle an extremely large number of droplets and microbes, thus suitable for screening large libraries of cells (FIG. 1).

The PolyChip system is capable of conducting polymicrobial interaction assays by directing co-culturing of 1) cells or microbes (or a single cell/microbe) that are potential producers of molecules that may influence a target microbe, and a 2) target cell or microbe, together inside a water-in-oil (or gel) emulsion droplet, followed by conducting a functional readout of how the produced molecules influence the target microbes, followed by sorting the potential "producer microbe", or "hit". Importantly, the PolyChip system enables continuous/semi-continuous operation of the entire process, which may include, but is not limited to, cell-encapsulated droplet generation, culture, merging with other cell-encapsulated droplets, co-culture, merging with reagent-laden droplets, incubation, followed by detection and sorting. Importantly, the order of operation of these steps can be varied to achieve desirable outcomes. The capabilities of continuous operation of the entire assay flow is critical when having to process extremely large numbers of droplets (e.g., multi-millions of cell-encapsulated droplets being processed over several tens of hours or even days), since otherwise cells in droplets undergo different culture periods in the various steps of the assay, resulting in different assay conditions for each of the cells. This feature is enabled through modular stacking of multiple functional components of the droplet microfluidic platform to create a new generation of integrated microfluidic system that allows continuous first-in first-out operation of complex assays. Here, the outlet of one functional module is connected to the inlet of a subsequent functional module, which is stacked on top (or below) of the first module, thus droplets will be moving continuously through each module. The volume of each module determines the resident time of droplets in each module for a given flow rate. This stacked design can be broadly employed in droplet microfluidic assays that require extremely large numbers of samples to be processed, where such operations can take several tens of hours (or even days or tens of days). Importantly, one or more of such modules may include a droplet incubation chamber that is large enough to hold larger number of droplets (e.g., hundreds of thousands, millions), but still allow continuous operation in a first-in first-out sequence.

In an embodiment, the PolyChip droplet microfluidic platform is fabricated by stacking individual layers of molded material into a single-chip structure. One embodiment of the PolyChip platform comprises, but not limited to, about 9 to 20 stacked layers. The individual layers may be made from PDMS, plastics, or other materials known in the art to be used in the construction of layered microfluidic devices. In an embodiment, the individual layers are formed using unique master molds designed to carve the network of channels and chambers through which fluid will pass during operation of the finished structure.

The master molds may be fabricated from a variety of materials known in the art. For example, silicon molds may be created by photolithography. Using this method, a desired pattern may be formed into a silicon wafer by treating the wafer with photoresist, and then exposing the wafer to UV light filtered through a photo mask. Alternatively, the master molds may be created from plastic using a 3D printing device or milling machine.

The Polychip droplet microfluidic platform may be fabricated by injection molding. In an embodiment, the platform is fabricated as a single injection molding piece. In an embodiment, multiple layers are fabricated as individual injection molding pieces that are stacked together and bonded.

The PolyChip microfluidic platform permits continuous/semi-continuous on-chip operation (FIG. 1). First, droplets comprising an aqueous medium (or gel) are continuously generated encapsulating a predetermined number of microbes, including select agents. The droplets travel through the PolyChip platform along the flow of an immiscible fluid. The movement of droplets in a continuous/semi-continuous manner maintains on-chip operation in first-in, first-out format.

Referring to FIG. 1, a conceptual framework of the on-chip assay is shown. A microfluidic platform 100 comprises a body 101 with a passage network and several chambers therein. The passage network includes an inlet passage 110, two connection passages 112 and 113. Two openings 130 and 131-132 are provided at the two ends of the inlet passage 110 to accommodate two droplet generators 132, 134 respectively. The droplet generators 132, 134 are mechanisms for continuous generation of cell-encapsulated droplets. A droplet generator can convert fluid into discrete droplets. In one embodiment, a fluid 140 containing environment microbes is delivered into the generator 134 and a fluid 141 containing target organisms is delivered into the generator 132. The generator 132 convert the target 141 into target droplets 142 and push them into the passage 110, the generator 134 convert the fluid 140 into microorganisms-containing droplets 143 and push them into the passage 110. When a droplet 142 and a droplet 143 meet in the middle of the passage 110, they can merge into an encapsulated droplet 144 wherein the microbe is encapsulated with the target organism. The encapsulated droplet 144 can be pushed into an incubation chamber 121 through the connection passage 112. The cells in the encapsulated droplet 144 can be incubated for a desired time period such that the encapsulated droplets 144 changes into incubated droplets 145. The time period can be controlled by the flow rate of the encapsulated droplet 144. The droplets 145 can be classified into three categories, the first category is growth enhanced droplet 146, the second category is growth inhibited droplet 147 and the third category is waste 148. After incubation, the incubated droplets 145 are pushed into the connection passage 113. In one embodiment, the connection passage 112 is near the head end of the incubation chamber 121 while the connection passage 113 is near the bottom end of the incubation chamber, such that the droplets in the incubation chamber 121 move in a first-in first-out manner to ensure the same incubation time for each of the droplet.

In one embodiment, a detection mechanism such as a LED detector 151 is provided to detect the droplets 145 flowing in the connection passage 113. The LED detector 151 can identify the growth enhanced droplet 146, the growth inhibited droplet 147 and the waste 148. The microfluidic platform 100 further comprises two collection chambers 122 and 123 to accommodate the growth enhanced droplet 146 and the growth inhibited droplet 147 respectively. Following the LED detector 151, two valves such as syringe pistons or pressure pulse generator 116 and 117 are located along the connection passage 113 and can cause pressure to push the growth enhanced droplet 146 and the growth inhibited droplet 147 off the connection passage 115 and into the collection chambers 122 and 123 separately, thus the growth enhanced droplet 146 and the growth inhibited droplet 147 can be analyzed respectively. The waste 148 can be discharged out of the connection passage 113.

Figure 2:
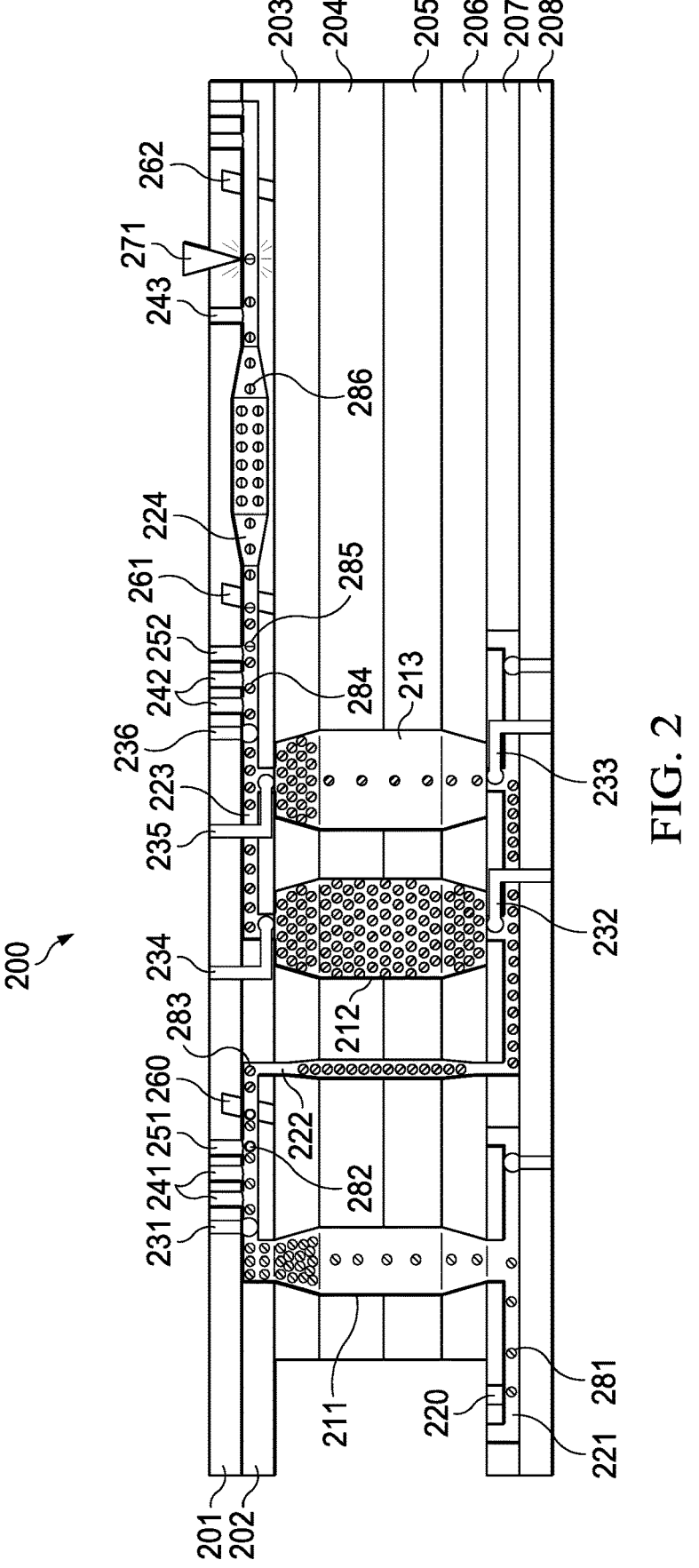
FIG. 2 Shows a droplet microfluidic PolyChip screening device in accordance with embodiments disclosed herein.
Figure 3:
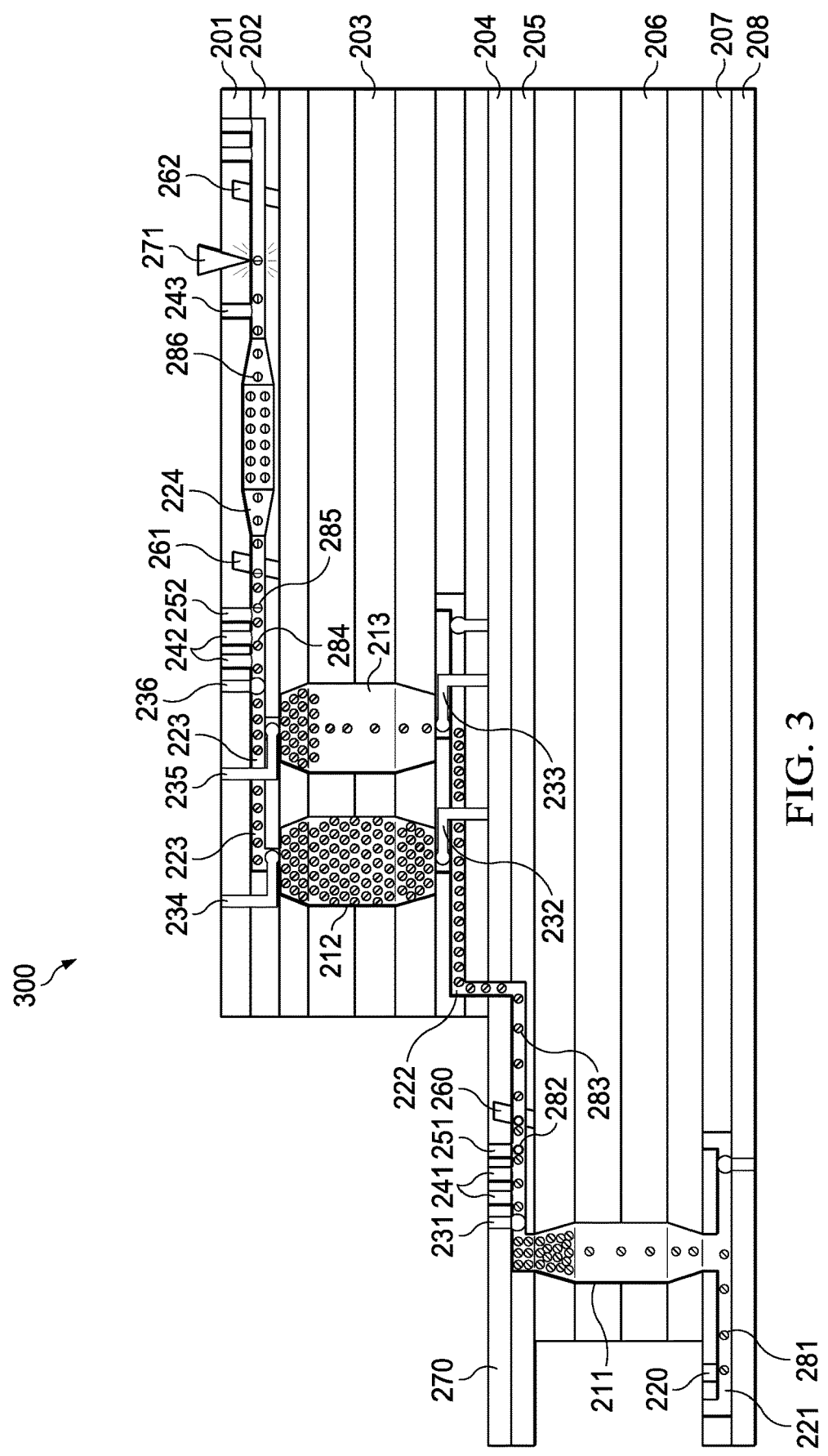
FIG. 3 Shows another droplet microfluidic PolyChip screening device in accordance with embodiments disclosed herein.

In some embodiments, the platform performs multi-stage on-chip incubation of droplets using a variety of functional components. Delay lines may be used as compartments for short-term incubations for up to a few hours. Alternatively, culture chambers that have larger volume than delay lines may be constructed to accommodate variable incubation times. For example, FIGS. 2 and 3 depict the PolyChip platforms incorporating culture chambers that incubate droplets from 30 minutes to 12 hours. In an embodiment, the incubation time can be adjusted from 12 to 72 hours. In an embodiment, the incubation time can be adjusted from 24 to 72 hours. The flow of droplets through the platform permits continuous operation in a first-in, first-out format to allow the same culture time for all droplets regardless of when the cell-encapsulated droplets are formed. The culture chambers are connected to the outlet of one or more droplet generators to allow sequential filling of each droplet-culture chamber. A large number of droplets may be trapped or released on demand into and out of the multiple droplet-culture chambers using integrated multi-layer valve structures. The culture duration may be changed via addition of layers through modular stacking or small design alterations to increase/decrease incubation volumes.

The platform integrates multi-stage 3D electrocoalescence-based merging of droplets containing different microbes/reagents/fluorescent markers/colorimetric markers to co-locate different samples within the same droplet.

The PolyChip platform includes an on-chip process for analyzing changes in cell-encapsulated droplets. In an embodiment, the process involves analyzing changes in the expression of nucleic acids (e.g., mRNA or rRNA) or proteins by target cells. In an embodiment, the process involves analyzing the production of metabolic products of target cells. In an embodiment, the process involves analyzing changes in the growth rate or occurrence of death, or apoptosis or necrosis in target cells. Detection mechanisms known in the art may be used for on-chip analysis of cell-encapsulated droplets. For example, analysis of fluorescent molecules may be performed using a compact 3D printed fluorescence detection system. Alternative on-chip detection mechanisms may be incorporated into the Poly-Chip platform, such as for analyzing colorimetric, dielectric (e.g., impedance spectroscopy), conductivity, or vibrational spectroscopy (e.g., Raman spectroscopy) signals.

Droplets containing microbes of interest, such as target cells exhibiting observable effects, may be sorted for further off-chip analyses. Sorted droplets are trapped using a basket trapping pillar structure capable of releasing droplets on demand. Recovery of sorted droplets may be accomplished by an on-chip or off-chip mechanism.

The layers of the PolyChip platform may be incorporated into a sandwich design (FIG. 2). Using this design, droplets are generated in the bottom layer, and then migrate into higher layers of the chip structure during operation (or alternatively e.g., gel droplets are generated in a top layer, and then migrate down to a lower layer during operation). In order to progress through the platform and to the next functional compartment, droplets are returned to a lower layer of the chip. This is accomplished by stacking droplets into a top-down format in a vertical channel leading to a lower layer. The droplets migrate to a higher layer during chip operation, and may be subsequently returned to a lower layer as needed. At conclusion of the chip operation, droplets are analyzed by a fluorescent detector and sorted.

Loom Referring to FIG. 2, in one embodiment, a Poly-Chip platform 200 includes multiple substrate layers, such as top substrate 201, bottom substrate 208 and middle substrates 202, 203, 204, 205, 206, 207 from the top down. A passage 221 is fabricated into the middle substrate 207 which is adjacent to the bottom substrate 208. The diameter of the passage 221 is about 45 µm, the inlet of an incubation chamber 211 is connected with the passage 221 to receive encapsulated droplet from the passage 221. The incubation chamber 221 extends through the middle substrates 202, 203, 204, 205, 206, 207 and has an outlet to connect a connection passage 222 which is fabricated into the middle substrate 202 adjacent to the top substrate 201. The diameter of the incubation chamber 211 is about 1.5 mm and the diameter of the connection passage 222 is about 200 µm. The connection passage 222 include a channel passage through the middle substrates 202, 203, 204, 205, 206, 207 from the top down and reach back to the substrate 207 to connect two inlets of incubation chambers 212 and 213 respectively such that the droplet in the connection passage 222 can be injected into the incubation chamber 212 or 213. Similar to the incubation chamber 211, the incubation chambers 212, 213 extend through the middle substrates 202, 203, 204,

205, 206, 207 and has outlets to connect a connection passage 223 which is fabricated into the middle substrate 202 adjacent to the top substrate 201. The PolyChip platform 200 includes a valve 231 at the outlet of the incubation chamber 211 to control the flow of the droplets therein. It also includes valves 232, 233, 234, 235 at the inlet and outlet of the incubation chambers 212 and 213 to control the flow of the droplets. The valves 231, 232, 233, 234, 235 are fabricated into the outer layers of the substrates such as substrates 201, 202 or substrates 207, 208 such that they be easily connected to outer control mechanism (e.g., pneumatic actuator, not shown), where the outer control mechanism can control the valve to open or close.

The passage 221 has an opening 220 to receive a first group of cell-encapsulated droplets 281. In one embodiment, the droplet 281 may include a first cell that can produce a molecule capable of affecting a target cell. Droplets 281 are pushed into the incubation chamber 211 through the passage 221. The cells in the droplets 281 are incubated in the incubation chamber 211 to produce the molecules that are accumulated within the droplets. The incubating time can be controlled by the flow rate of the encapsulated droplets in the passage 221, or it can also be controlled by the valve 231, where the valve 231 can open or close the outlet of the incubation chamber 211. In one embodiment, the incubating time is 12 hours. After incubating, the droplets 281 are pushed into the connection passage 222, along the connection passage 222. The PolyChip platform 200 provide two spacing mechanisms 241 to separate the droplets 281 to make each of the droplets 281 to keep a certain distance between them. The connection passage 222 is then connected to a deliver channel 251, and a second group of cell-encapsulated droplets 282 can be delivered into the connection passage 222 through the deliver channel 251. In one embodiment, the droplet 282 may include a target cell.

The PolyChip platform 200 includes a merging mechanism 260 coupled with the connection passage 222 to merge droplet 282 and droplet 281. In order to increase the droplet merging efficiency, the merging mechanism 260 is a mechanism for multi-stage 3D electrocoalescence-based merging of droplets. The model of the mechanism can be found in A. R. Guzman et al. "HIGHLY EFFICIENT ELECTROCOALESCENCE-BASED DROPLET MERGING USING A 3D ELECTRODE", 18th International Conference on Miniaturized Systems for Chemistry and Life Sciences, Oct. 26-30, 2014, San Antonio, Texas, USA, pages 1220 to 1222, which is herein incorporated by reference in its entirety.

After the droplet 282 and droplet 281 merge into a droplet 283, the droplet 283 moves from top to bottom of the PolyChip platform 200 along the channel of the passage 222 and enters into incubation chamber 212 or incubation chamber 213. The droplet 283 can selectively enter into incubation chamber 212 or incubation chamber 233 by selectively opening or closing the valve 232 and 233. In some embodiments, the incubating time in the incubation chamber 212 is 12 hours and the incubating time in the incubation chamber 212 is 30 minutes. The droplet 283 includes the first cell, the target cell, and molecules produced by the first cell. During the period of incubation, the molecules can influence the target cell, the droplet 283 is incubated into a droplet 284. By selectively opening or closing the valve 234 and 235, the droplet 284 can be pushed out of incubation chamber 212 or incubation chamber 233 and enters into a connection passage 223.

In some embodiments, the droplets 284 in the connection passage 223 can be spaced by a spacing mechanism 243 and then be detected by an on-chip detection mechanism 271 which is coupled with the connection passage 223. In one embodiment, the on-chip detection mechanism 271 can detect optical, dielectric, conductivity, or vibrational spectroscopy signals of the droplets 284. In some embodiments, the optical detection mechanism comprises fluorescence or colorimetry, the dielectric detection mechanism comprises impedance spectroscopy, the vibrational spectroscopy signal comprises Raman spectroscopy or infrared spectroscopy.

Based on the result of the detection, a mechanism 262 for sorting of the droplets 284 is used to trap detected droplets 284 into different recovery chamber. The mechanism 262 can be a syringe piston 116 in FIG. 1, the recovery chamber can be an on-chip chamber 122 in FIG. 1 (with on-demand releasing and spacing capabilities) or an off-chip chamber.

In some embodiments, referring back to FIG. 2, before being detected, the droplets 284 need to be merged with a third group of cell-encapsulated droplets 285. To implement the merging, two spacing mechanisms 242 are provided to separate the droplets 281 to make each of the droplets 281 to keep a certain distance. The connection passage 223 is then connected to a deliver channel 252, and a third group of cell-encapsulated droplets 285 can be delivered into the connection passage 223 through the deliver channel 252. A merging mechanism 261 can merge droplet 284 and droplet 285 into a droplet 286. The droplet 286 then flow into a large serpentine channel 224. The serpentine channel 224 can prolong residence time of the droplet 286 therein to provide enough incubating time of the droplet 286. The incubating time can be controlled by the flow rate of the droplets 286 in the passage serpentine channel 224. Following the step of incubation, the droplet 286 can be detected and sorted.

In some embodiments, the layers of the PolyChip platform may alternatively be incorporated into a stacked design (FIG. 3). Similar to the sandwich design, droplets are generated in a lower layer, and then migrate into higher layers of the chip structure during operation. The stacked design arranges the functional components so that droplets migrate into progressively higher layers of the chip structure during operation. Droplets are not required to migrate to lower layers of the chip structure for continued on-chip operation. At conclusion of chip operation, droplets are analyzed by a fluorescent detector and sorted. The stacked design has the ability to eliminate (or minimize) the possibility for dead volume and is more suitable for semi-continuous operation, whereas the sandwich design is more suitable for continuous operation. Both designs utilize the buoyancy effect of droplets in oil, where depending on the selection of carrier oil, droplets either naturally float or naturally sink.

Referring to FIG. 3, a PolyChip platform 300 includes multiple substrate layers and functional components similar to the functional components in FIG. 2. The platform 300 includes more substrate layers than the platform 200 in order to accommodate incubation chambers 211,212 and 213 that are not in the same horizontal plane. The incubation chambers 212 and 213 and their control components such as valves 234, 235, spacing mechanisms 242 are in the higher substrate layers 201,202,203. The incubation chamber 211 with its control components such as valve 231, spacing mechanisms 241, deliver channel 251, merging mechanism 260 are located in the lower substrate layers 204,205,206, 207 and 208. In order to allow the control components of incubation chamber 211 to have access to the outside of the platform 300 easily, the control components should not be covered by the higher substrate layers. The areas of the lower substrate layers are bigger than areas of the higher substrate layers such that the part 270 of the lower substrate layer 204 is not covered by the higher substrate layers. The control components of incubation chamber 211 are fabricated in the part 270 of the lower substrate layer 204 and can be easily communicated with the outside of the platform 300. A connection passage 222 connects the incubation chamber 211 with the incubation chambers 212, 213. The operation of droplets using the PolyChip platform 300 is similar to the operation process using the PolyChip platform 200 as mentioned above.

The PolyChip platform is not limited to operations explicitly described herein. The device is compatible with any operational features known in the art that are not explicitly described herein. Applicability of the device for other features is dependent only on the ability of the user to design the PDMS layers of the platform in such a way to accommodate the desired feature.

The developed PolyChip system can be developed into a commercially available high-throughput screening system. In addition, it can lead to a service provider for high-throughput screening to screen libraries of interest for biologists, agencies, researchers, or companies.

Current conventional methods for the analysis of complex cellular (or microbial) interactions require time-consuming manual or robotic operations using multi-well cell culture plates. With the use of the developed PolyChip and similar systems, the identification of cellular (or microbial) interactions and the development of anti-microbial, anti-virulence, anti-fungal, or anti-select agent compounds can be drastically improved by reducing the time it takes to conduct such studies by several orders of magnitude and reducing the overall cost of such screening assays. In addition, the analysis of microbiome dynamics, including microbiome-host interactions, can be facilitated. Utilizing droplet microfluidics allows the manipulation of pico-liter volume samples, reducing the reagent consumption by 6 orders of magnitude, which can greatly reduce the experiment cost. Experiments which previously took months or years will only require hours to days to conduct at a fraction of the cost.

EXAMPLES

Example 1 Fabrication of the PolyChip Microfluidic Platform with PDMS Layers In an embodiment, master molds for each layer are fabricated using photolithography and 3D printing/milling technologies known in the art. Silicon molds can be created by spincoating photoresist on the surface of a silicon wafer. The molds are exposed to UV light filtered through a photo mask to imprint the desired pattern. Alternatively, 3D master molds can be printed using a 3D printer, such as an Envision Tec Ultra LS 3D printer. Alternatively, 3D plastic molds can be milled by a milling machine, such as a Roland MDX-50 Benchtop CNC.

In an embodiment, master molds are coated with trichlorosilane in preparation for PDMS fabrication. Liquid PDMS is mixed 10:1 with curing agent, poured into the master mold, and baked at 85° C. for 1 hour. The cured PDMS is removed and holes are punched for tubing interface connections. The individual PDMS layers are then aligned using methanol and bonded with oxygen plasma. The PolyChip platform comprises of about 9 to about 20 stacked layers. Finally, the device is baked at high temperature or coated with Aquapelhydrophobic surface coating to make the PDMS surface hydrophobic, where hydrophobicity of PDMS is necessary for droplet microfluidics operation. Other chemicals known in the art may be utilized for this purpose.

Example 2 PolyChip Fabrication Using the Sandwich Design

The layers of the PolyChip platform may be incorporated into a sandwich design (FIG. 2). Using this design, droplets are generated in the bottom layer and floated up to the top layer where a second droplet is generated. The droplets may be synchronized and merged in the top layer. Merged droplets are then stacked using a top-down format and directed to the bottom layer where they are incubated again. The merged droplets are floated back to the top layer, where a third droplet may be generated, synchronized, and merged. Finally, resultant droplets are analyzed by a fluorescent detector and sorted.

Example 3 PolyChip Fabrication Using the Stacked Design

The layers of the PolyChip platform may alternatively be incorporated into a stacked design (FIG. 3). Similar to the sandwich design, droplets are generated in the bottom layer, floated up to the top layer where a second droplet is generated, synchronized, and merged. However, merged droplets are floated and incubated into a higher layer, rather than stacking top-down to a bottom layer. A third series of droplets may be generated, synchronized, and merged with the previous droplets. The resultant droplets are analyzed by a fluorescent detector and sorted.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain materials and agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A droplet microfluidic platform comprising:
a plurality of substrate layers, and
a plurality of functional components,
wherein the plurality of substrate layers is configured such that, when the plurality of substrate layers are stacked, one or more of the plurality of functional components is collectively formed within two or more of the plurality of substrate layers, the functional components comprising:
at least one droplet generator for continuous generation of cell-encapsulated droplets;
at least one merging mechanism configured to merge the cell-encapsulated droplets;
at least two incubation chambers for on-chip incubation of the cell-encapsulated droplets;
at least a first valve for trapping or releasing the cell-encapsulated droplets;

13

14 a detection mechanism; and a second valve configured to direct the cell-encapsulated droplets from a first of the at least two incubation chambers to a second of the at least two incubation chambers;

at least one fluid passage to connect the functional components;

wherein the platform is capable of continuous/semi-continuous on-chip operation in a first-in first-out manner, wherein the platform comprises a sandwich design, wherein the at least two incubation chambers are in a same horizontal plane, wherein the at least two incubation chambers are configured such that the cell-encapsulated droplets move out of one of the at least two incubation chambers and travels vertically from a higher substrate layer of the platform to a lower layer of the platform to enter into another incubation chamber of the at least two incubation chambers, wherein the platform is configured such that the cell-encapsulated droplets travel vertically from a lower layer of the platform to a higher layer of the platform.

2. The droplet microfluidic platform of claim 1, further comprising a chamber configured to provide for on-chip recovery of the cell-encapsulated droplets.

3. The droplet microfluidic platform of claim 1, wherein the detection mechanism is configured to detect an optical, dielectric, conductivity, or vibrational spectroscopy signal.

4. The droplet microfluidic platform of claim 1, wherein the substrate layers comprises about 9 to about 20 polydimethylsiloxane layers.

5. A method of producing the droplet microfluidic platform of claim 1, the method comprising:

casting about 9 to about 20 individual polydimethylsiloxane layers from master molds;

bonding the individual polydimethylsiloxane layers into a single structure utilizing corresponding integrated alignment methods imbedded into each layer, comprising the functional components between adjacent layers; and wherein the platform is capable of continuous/semi-continuous on-chip operation through a sequence of the functional components in a first-in first-out manner.

6. A method of producing the droplet microfluidic platform of claim 1 comprising:

injection molding the substrate layers of the platform as individual pieces;

bonding the individual pieces into a single structure comprising the functional components between adjacent layers; and wherein the platform is capable of continuous/semi-continuous on-chip operation through a sequence of the functional components in a first-in first-out manner.

7. A method of producing the droplet microfluidic platform of claim 1 comprising:

injection molding the sandwich design into a single component; and wherein the platform is capable of continuous/semi-continuous on-chip operation through a sequence of the functional components in a first-in first-out manner.

8. A method for identifying cell-produced molecules affecting a target cell utilizing the droplet microfluidic platform of claim 1, comprising:

generating continuously a first group of cell-encapsulated droplets from a library of cells that are potential producers of the cell-produced molecules that are capable of affecting the target cell;

incubating the first group of the cell-encapsulated droplets to provide time for the molecules produced by the cells to accumulate;

generating a second group of cell-encapsulated droplets containing the target cells;

merging of the first and second groups of cell-encapsulated droplets to allow co-incubation of both cell types and to provide time for the produced molecules to influence the target cells;

analyzing the cell-encapsulated droplets using the detection mechanism;

sorting the cell-encapsulated droplets; and recovering the sorted cell-encapsulated droplets.

9. The method of claim 8 wherein the recovering of the sorted cell-encapsulated droplets is on-chip, wherein the on-chip analysis of the cell-encapsulated droplets comprises of at least one selected from the group consisting of:

determining expression or function of a nucleic acid or protein;

analyzing the growth rate, death, necrosis or apoptosis of the target cells; and evaluating metabolic activity or production of metabolic products.

10. The method of claim 9 wherein the detection mechanism is configured for the detection of fluorescent, colorimetric, dielectric, conductivity, or vibrational spectroscopy signals.

11. A droplet microfluidic platform, comprising:

a plurality of substrate layers, and a plurality of functional components, wherein the plurality of substrate layers is configured such that, when the plurality of substrate layers are stacked, one or more of the plurality of functional components is collectively formed within two or more of the plurality of substrate layers, the functional components comprising:

at least one droplet generator for continuous generation of cell-encapsulated droplets;

at least one merging mechanism configured to merge the cell-encapsulated droplets;

at least two incubation chambers for on-chip incubation of the cell-encapsulated droplets;

at least a first valve for trapping or releasing the cell-encapsulated droplets;

a detection mechanism; and a second valve configured to direct the cell-encapsulated droplets from a first of the at least two incubation chambers to a second of the at least two incubation chambers;

at least one passage to connect the functional components;

wherein the platform is capable of continuous/semi-continuous on-chip operation in a first-in first-out manner, wherein the platform comprises a stacked design, wherein the at least two incubation chambers are in different horizontal planes, wherein at least one of the at least two incubation chambers is located in higher substrate layers and at least one of the at least two incubation chambers is located in lower substrate layers, wherein the platform is configured such that the cell-encapsulated droplets traverse the platform vertically from a lower layer of the platform to a higher layer of the platform.

12. The droplet microfluidic platform of claim 11, further comprising a chamber configured to provide for on-chip recovery of the cell-encapsulated droplets.

13. The droplet microfluidic platform of claim 11, wherein the detection mechanism is configured to detect an optical, dielectric, conductivity, or vibrational spectroscopy signal.

14. The droplet microfluidic platform of claim 11, wherein the substrate layers comprises about 9 to about 20 polydimethylsiloxane layers.

15. A method of producing the droplet microfluidic platform of claim 11, the method comprising:

casting about 9 to about 20 individual polydimethylsiloxane layers from master molds;

bonding the individual polydimethylsiloxane layers into a single structure utilizing corresponding integrated alignment methods imbedded into each layer, comprising the functional components between adjacent layers; and wherein the platform is capable of continuous/semi-continuous on-chip operation through a sequence of the functional components in a first-in first-out manner.

16. A method of producing the droplet microfluidic platform of claim 11 comprising:

injection molding the substrate layers of the platform as individual pieces;

bonding the individual pieces into a single structure comprising the functional components between adjacent layers; and wherein the platform is capable of continuous/semi-continuous on-chip operation through a sequence of the functional components in a first-in first-out manner.

17. A method of producing the droplet microfluidic platform of claim 11 comprising:

injection molding the stacked design into a single component; and wherein the platform is capable of continuous/semi-continuous on-chip operation through a sequence of the functional components in a first-in first-out manner.

18. A method for identifying cell-produced molecules affecting a target cell utilizing the droplet microfluidic platform of claim 11, comprising:

generating continuously a first group of cell-encapsulated droplets from a library of cells that are potential producers of the cell-produced molecules that are capable of affecting a target cell;

incubating the first group of the cell-encapsulated droplets to provide time for the molecules produced by the cells to accumulate;

generating a second group of cell-encapsulated droplets containing the target cells;

merging of the first and second groups of cell-encapsulated droplets to allow co-incubation of both cell types and to provide time for the produced molecules to influence the target cells;

analyzing the cell-encapsulated droplets using the detection mechanism;

sorting the cell-encapsulated droplets; and recovering the sorted cell-encapsulated droplets.

19. The method of claim 18 wherein the recovering of the sorted cell-encapsulated droplets is on-chip, wherein the on-chip analysis of the cell-encapsulated droplets comprises of at least one selected from the group consisting of:

determining expression or function of a nucleic acid or protein;

analyzing the growth rate, death, necrosis or apoptosis of the target cells; and evaluating metabolic activity or production of metabolic products.

20. The method of claim 18 wherein the detection mechanism is configured for the detection of fluorescent, colorimetric, dielectric, conductivity, or vibrational spectroscopy signals.

* * * * *